US010895920B2

United States Patent
K-Laflamme

(10) Patent No.: US 10,895,920 B2
(45) Date of Patent: Jan. 19, 2021

(54) PNEUMATICALLY ACTUATED COMPUTER INPUT DEVICE

(71) Applicant: Eric K-Laflamme, Quebec (CA)

(72) Inventor: Eric K-Laflamme, Quebec (CA)

(*) Notice: Subject to any disclaimer, the term of this patent is extended or adjusted under 35 U.S.C. 154(b) by 543 days.

(21) Appl. No.: 14/542,557

(22) Filed: Nov. 15, 2014

(65) Prior Publication Data

US 2015/0142184 A1 May 21, 2015

(30) Foreign Application Priority Data

Nov. 15, 2013 (GB) .................................. 1320238.7

(51) Int. Cl.

| | |
|---|---|
| *G05D 11/00* | (2006.01) |
| *G06F 3/033* | (2013.01) |
| *G06F 3/0354* | (2013.01) |
| *G05D 7/06* | (2006.01) |
| *G06F 3/01* | (2006.01) |
| *G05B 15/02* | (2006.01) |

(Continued)

(52) U.S. Cl.
CPC ........... *G06F 3/0334* (2013.01); *G05B 15/02* (2013.01); *G05D 7/06* (2013.01); *G05D 7/0623* (2013.01); *G05D 7/0629* (2013.01); *G06F 3/01* (2013.01); *G06F 3/03543* (2013.01); *A61B 1/24* (2013.01); *G06F 3/03* (2013.01)

(58) Field of Classification Search
CPC .......... G06F 3/014; G06F 3/03; G06F 3/0334; G08C 19/16; A61M 5/14566; A61M 19/00; A61C 1/0023; A61C 1/0007; A61C 3/025; A61C 19/004; A61C 9/004; A61C 17/02; A61C 17/20; A61B 6/04; A61G 15/02; G05B 15/02; G05D 7/06; G05D 7/0623; G05D 7/629
See application file for complete search history.

(56) References Cited

U.S. PATENT DOCUMENTS 4,114,275 A * 9/1978 Jones ................... A61C 1/0023
433/101
5,126,731 A   6/1992 Cromer et al.
(Continued)

FOREIGN PATENT DOCUMENTS

| | | |
|---|---|---|
| CN | 201859412 | 6/2011 |
| EP | 1714617 | 10/2006 |

(Continued)

*Primary Examiner* — Tuan A Vu

(57) ABSTRACT

A pneumatically actuated computer input device comprises an input device circuit member having a hollow body, at least one switch member within the hollow body adapted to send electronic signals to a computer terminal, and a pneumatic actuator within the hollow body adapted to be inflated and press against and activate the at least one switch member. A pneumatic hose connected at a distal end to the pneumatic actuator and extending outward from the hollow body at a predetermined length and adapted to supply air thereto, and a foot pedal connected to the pneumatic hose at an opposite end from the distal end and adapted to control the air supply through the pneumatic hose and to the pneumatic actuator, such that when the foot pedal is pressed the pneumatic actuator is filled with air, expands, and presses against the at least one switch member which then sends an electronic signal to the computer terminal.

12 Claims, 5 Drawing Sheets

(51) Int. Cl.
*A61B 1/24* (2006.01)
*G06F 3/03* (2006.01)

(56) References Cited

U.S. PATENT DOCUMENTS

| | | | |
|---|---|---|---|
| 5,422,521 A | 6/1995 | Neer et al. | |
| 5,745,055 A | 4/1998 | Redlich et al. | |
| 5,861,870 A | 1/1999 | Anderson | |
| 5,907,318 A | 5/1999 | Medina | |
| 6,022,337 A * | 2/2000 | Herbst | A61M 5/14566 604/131 |
| 6,325,624 B1 * | 12/2001 | Kutsch | A61C 3/025 433/116 |
| 6,574,571 B1 | 6/2003 | Bonnat | |
| 6,652,482 B2 * | 11/2003 | Hochman | A61M 19/00 604/118 |
| 6,798,396 B2 | 9/2004 | Gemunder et al. | |
| 7,369,116 B2 | 5/2008 | Logue | |
| 7,422,432 B2 | 9/2008 | Warner | |
| 7,781,941 B2 | 8/2010 | Harvath et al. | |
| 8,723,668 B1 * | 5/2014 | Strohallen | A61G 15/02 340/12.5 |
| 2004/0115591 A1 * | 6/2004 | Warner | A61C 1/0023 433/98 |
| 2004/0183352 A1 * | 9/2004 | Schron | A61C 1/0007 297/323 |
| 2004/0185413 A1 * | 9/2004 | Gill | A61C 19/004 433/29 |
| 2010/0013767 A1 * | 1/2010 | Gu | G06F 3/014 345/158 |
| 2011/0104634 A1 * | 5/2011 | Kyostila | A61B 6/04 433/29 |
| 2012/0301844 A1 * | 11/2012 | Guaragno | A61C 17/20 433/101 |
| 2014/0266636 A1 * | 9/2014 | Larsen | G08C 19/16 340/12.5 |
| 2014/0272767 A1 * | 9/2014 | Monty | A61C 9/004 433/27 |
| 2015/0010882 A1 * | 1/2015 | Bergheim | A61C 17/02 433/80 |

FOREIGN PATENT DOCUMENTS

| | | |
|---|---|---|
| GB | 2338052 | 12/1999 |
| GB | 2467009 | 7/2010 |
| WO | WO0048066 | 8/2000 |
| WO | WO 2005060859 | 7/2005 |

* cited by examiner

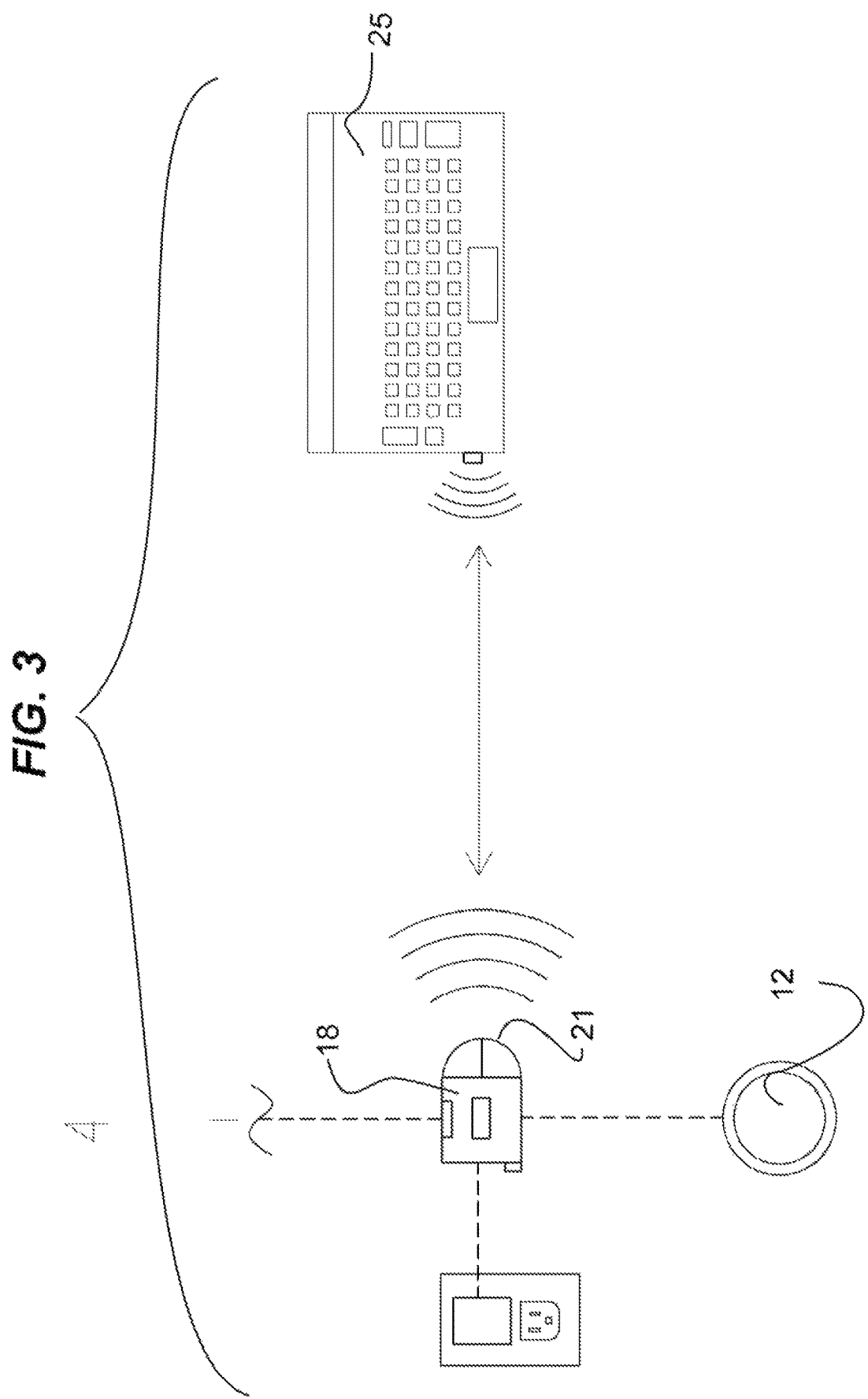

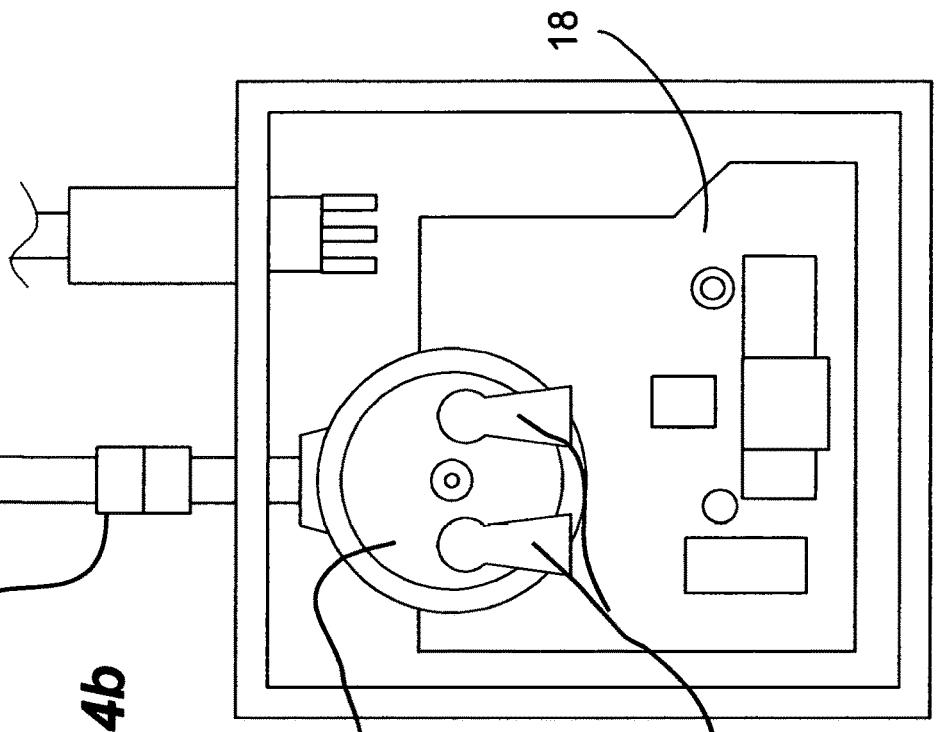
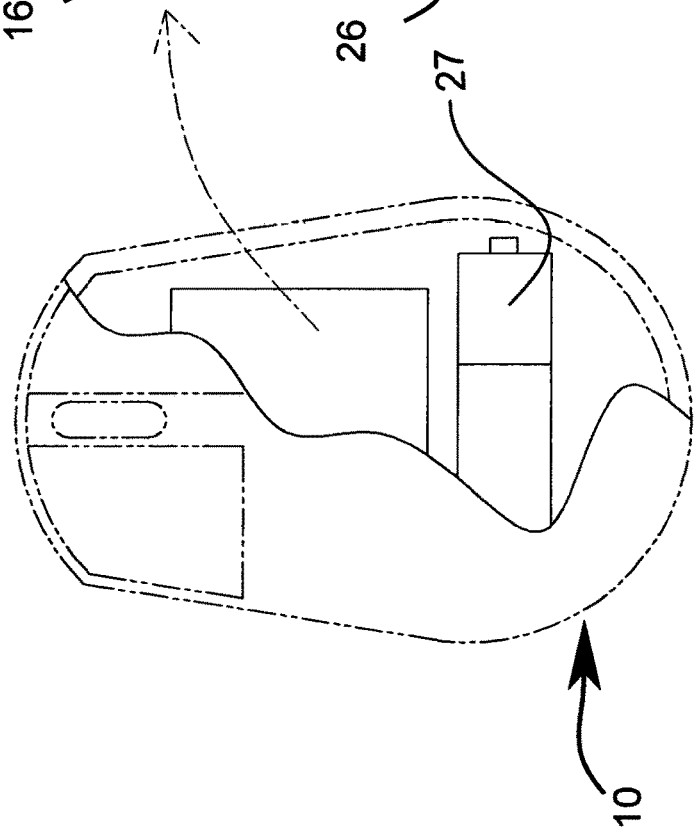
FIG. 4b
FIG. 4a

PNEUMATICALLY ACTUATED COMPUTER INPUT DEVICE

FIELD OF THE INVENTION

The present invention relates generally to computer input interface but more particularly to a pneumatically actuated computer input device.

BACKGROUND OF THE INVENTION

Dentists rely increasingly on the use of computers in their practice. It can be for imagery purposes such as taking photos or videos of a patient's mouth, for example. The problem is in how to computer can be made to do an action while the dentist has his hands busy without having to add a second pneumatic or electronic pedal, as each added piece of equipment makes keeping the room aseptic more complicated.

SUMMARY OF THE INVENTION

It is a main advantage of this invention to provide for an easy way for a dentist to operate a computer input device such as a mouse or game port device that is used for controlling various devices such as an intra oral camera by simply using a foot pedal which controls the flow of a pneumatic hose. The air pressure presses down on a switch on a computer input device circuit. Pneumatic pedals are well known in the art of dentistry and controlling a switch using air makes it easy for dentists to learn how to use the device. Generally, dentists use a foot pedal to actuate certain tools such as a pneumatic drill for example. The response to a switch can be programmed by existing software. For example, a click can actuate a macro that opens a video application. A double click can actuate another macro. These macros can be re-initialised quickly by redefining the action that a click (or double click, or click and hold) can do so as to allow pre defined functions depending on the task to be performed on a specific patient.

Each press on the pedal that controls the pneumatic hose presses on a switch which sends a signal is sent to the computer. If the computer software is in "stop" mode, the signal will have no effect. When the software is "on", each received signal effects a function. For example, if a dentist wants to use a drill while at the same time taking pictures with an intra oral camera, all he has to do is put the software on and each time he stops and restarts the drill, by releasing and pressing the pedal, a picture is taken (or a video clip). The dentist does not have to choose with a pedal click if he will use the drill or any other air instrument, since each pedal click is sent to the computer no matter what he wants to do.

If no other action programmed in the computer is needed, all the dentist has to do is to put the software in "off" (or pause, stop).

In order to do so, the invention comprises an input device circuit member having a hollow body, at least one switch member within the hollow body adapted to send electronic signals to a computer terminal, and a pneumatic actuator within the hollow body adapted to be inflated and press against and activate the at least one switch member. A pneumatic hose connected at a distal end to the pneumatic actuator and extending outward from the hollow body at a predetermined length and adapted to supply air thereto, and a foot pedal connected to the pneumatic hose at an opposite end from the distal end and adapted to control the air supply through the pneumatic hose and to the pneumatic actuator, such that when the foot pedal is pressed the pneumatic actuator is filled with air, expands, and presses against the at least one switch member which then sends an electronic signal to the computer terminal.

The pneumatically actuated computer further comprises a power source to provide electricity to the input device circuit member, which is then used to send the electronic signals.

The pneumatically actuated computer has the power source formed as an AC (alternating current) power source.

The pneumatically actuated computer has the power source comprising battery member.

The pneumatically actuated computer input has the input device circuit member further comprising an electrical wire connected to the at least one switch member and is adapted to connect with the computer terminal, to thereby send electronic signals to the computer terminal.

The pneumatically actuated computer input is further comprised of a signal receiver adapted to be connected to the computer terminal, and the input device circuit member id further comprised of a signal transmitter connected to the at least one switch member that is adapted to wirelessly connect with the signal receiver on the computer terminal, to thereby wirelessly send electronic signals to the computer terminal.

The pneumatically actuated computer input has the pneumatic hose being pass through so as to have an entry point into the input device different than an exit point.

The pneumatically actuated computer device is comprised of a computer terminal and a pneumatically actuated computer input device. Since pneumatically actuated triggers (pedals) are known in the art and that the circuitry of an input device for a computer is also known in the art, no discussion about these components is given since they are known in different arts.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways.

Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. For example, although described primarily as a tool for dentists, it should be understood that such a device can be used by other professionals or artisans. Such a device could also be used by people having reduced mobility. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and

BRIEF DESCRIPTION OF THE DRAWINGS

FIG. 3 Top view of the invention.

FIGS. 4a-b Top views of an input device with micro switch.

DETAILED DESCRIPTION

Figure 1:
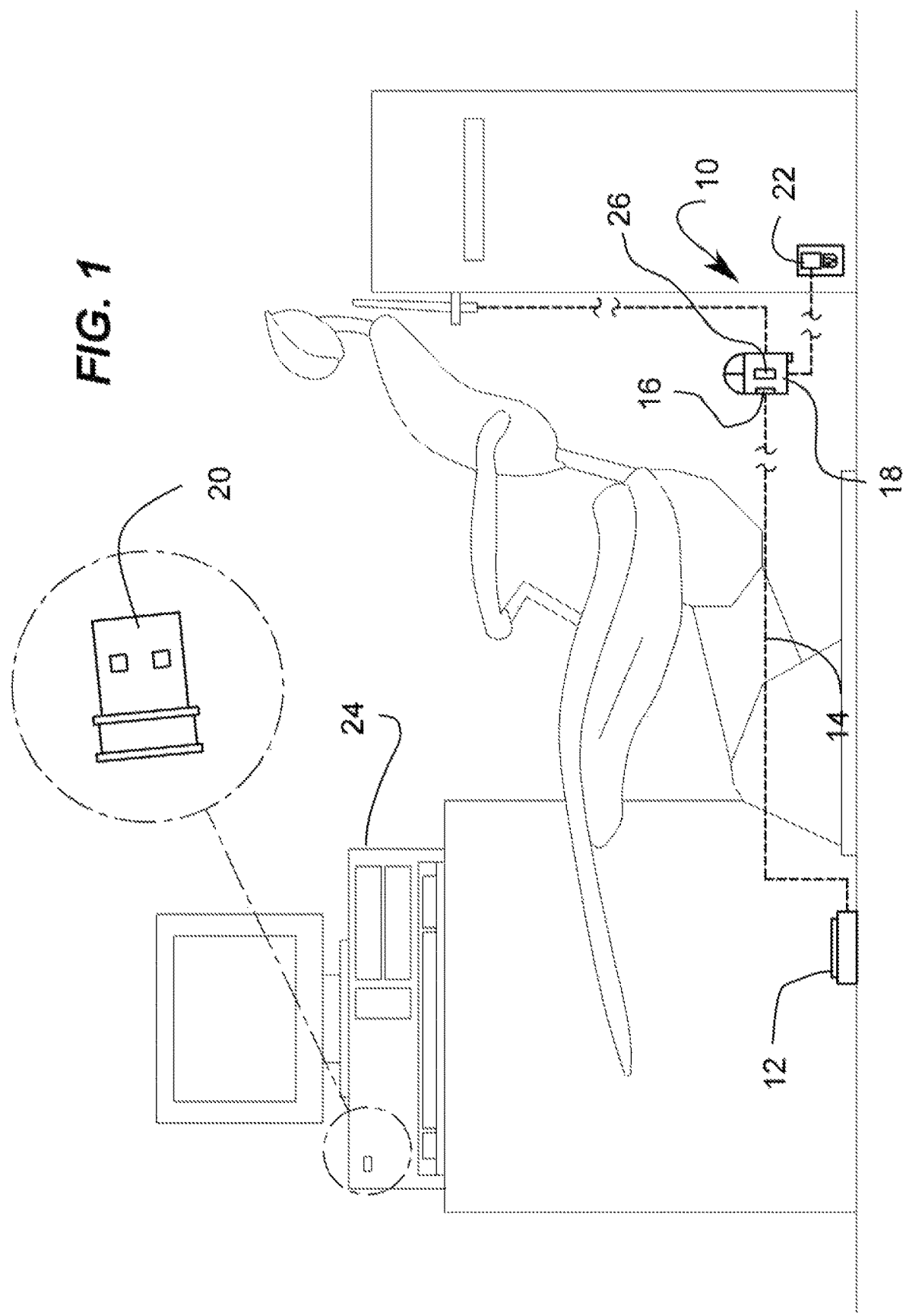
FIG. 1 Side elevation of the invention in context of use.
Figure 2:
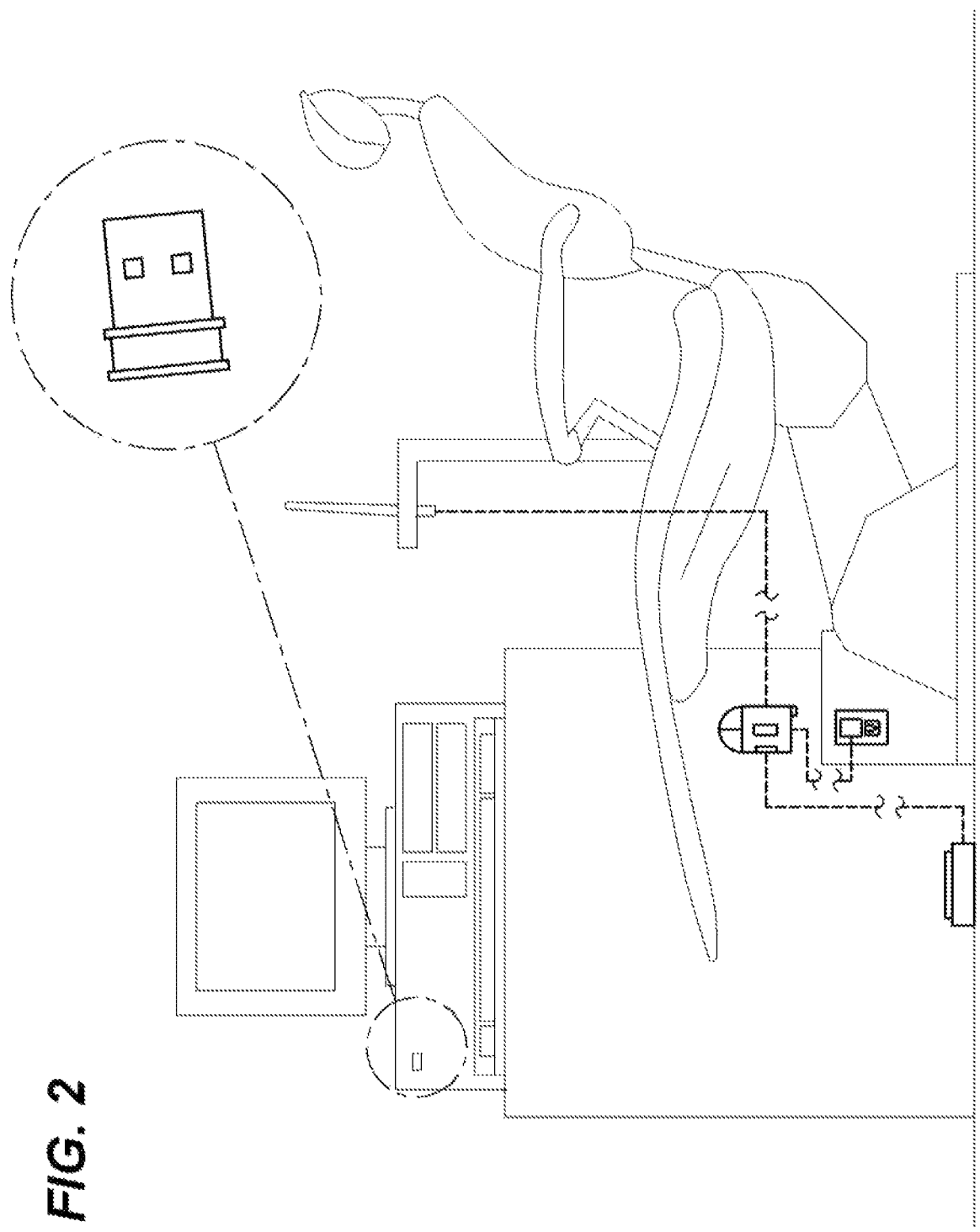
FIG. 2 Side elevation of the invention in context of use with an alternate air hose configuration.

A pneumatically actuated computer input device (10) is actuated by a foot pedal (12). The foot pedal (12) itself controls the flow of pressurized air inside a pneumatic hose (14). The pressure inflates a pneumatic actuator (16) which then presses down on a switch member (26) located on the input device circuit member (18). Once a click is made (or any combination thereof), the rest works like a usual input device click—including macros—whether the input device circuit (18) is wireless,—in which case a signal receiver (20) connected to a computer (24), or keyboard (25) is required—or wire based (not shown). The input device circuit member (18) is generally connected to a power source such as an AC source (22) for example, or a DC source such as a battery member (27), for example. The input device circuit member (18) also comprises a signal transmitter (21) to communicate with the signal receiver (20).

Figure 5:
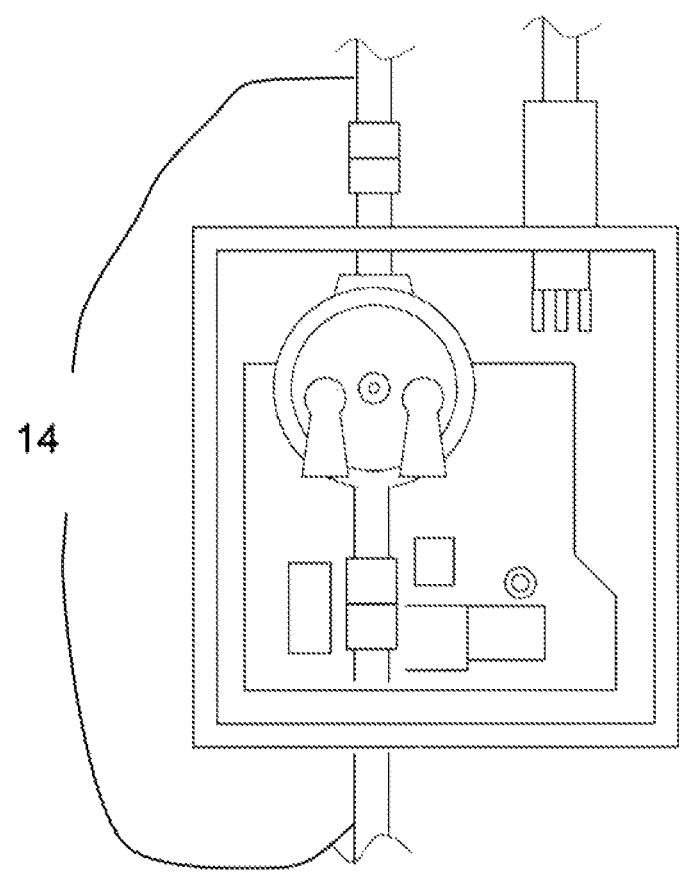
FIG. 5[a] Top view of a variant of the input device wherein the air hose has an entry and an exit point.

FIG. 5 shows a variant, the input device member (18) wherein the pneumatic hose (14) is a pass through hose having an entry point into the input device (10) different than the exit point so as to operate another device such as those available in the dentistry industry.

The invention claimed is:

1. A pneumatically actuated computer input device which is actuated by a foot pedal itself controlling the flow of pressured air inside a pneumatic hose, comprising an input device circuit member having a hollow body, at least one switch member within said hollow body adapted to send electronic signals to a computer terminal, and a pneumatic actuator within said hollow body adapted to be inflated and press against and activate said at least one switch member; wherein said pneumatic hose is connected at a distal end to said pneumatic actuator and extends outward from said hollow body at a predetermined length and adapted to supply pressured air thereto; and wherein said foot pedal is connected to said pneumatic hose at an opposite end from said distal end and adapted to control said pressured air supply through said pneumatic hose and to said pneumatic actuator, such that when said foot pedal is pressed the pneumatic actuator is filled with pressured air, expands, and presses against said at least one switch member which then sends an electronic signal to said computer terminal, and the pneumatic tool is actuated simultaneously.

2. The pneumatically actuated computer input device of claim 1, further comprising a power source to provide electricity to said input device circuit member, which is then used to send said electronic signals.

3. The pneumatically actuated computer input device of claim 2, wherein said power source is AC (alternating current).

4. The pneumatically actuated computer input device of claim 2, wherein said power source is DC (direct current).

5. The pneumatically actuated computer input device of claim 1, wherein said input device circuit member further comprises an electrical wire connected to said at least one switch member and is adapted to connect with said computer terminal, to thereby send electronic signals to said computer terminal.

6. The pneumatically actuated computer input device of claim 1, further comprising a signal receiver adapted to be connected to said computer terminal; and wherein said input device circuit member further comprises a signal transmitter connected to said at least one switch member that is adapted to wirelessly connect with said signal receiver on said computer terminal, to thereby wirelessly send electronic signals to said computer terminal.

7. A pneumatically actuated computer device comprising a computer terminal and a pneumatically actuated computer input device which is actuated by a foot pedal itself controlling the flow of pressured air inside a pneumatic hose, said pneumatically actuated computer input device comprising an input device circuit member having a hollow body, at least one switch member within said hollow body adapted to send electronic signals to said computer terminal, and a pneumatic actuator within said hollow body adapted to be inflated and press against and activate said at least one switch member; wherein said pneumatic hose is connected at a distal end to said pneumatic actuator and extends outward from said hollow body at a predetermined length and adapted to supply pressured air thereto; and wherein said foot pedal connected to said pneumatic hose at an opposite end from said distal end and adapted to control said pressured air supply through said pneumatic hose and to said pneumatic actuator, such that when said foot pedal is pressed the pneumatic actuator is filled with pressured air, expands, and presses against said at least one switch member which then sends an electronic signal to said computer terminal, and the pneumatic tool is actuated simultaneously.

8. The pneumatically actuated computer input device of claim 7, further comprising a power source to provide electricity to said input device circuit member, which is then used to send said electronic signals.

9. The pneumatically actuated computer input device of claim 8, wherein said power source is AC (alternating current).

10. The pneumatically actuated computer input device of claim 8, wherein said power source is DC (direct current).

11. The pneumatically actuated computer input device of claim 7, wherein said input device circuit member further comprises an electrical wire connected between said at least one switch member and said computer terminal, to thereby send electronic signals to said computer terminal.

12. The pneumatically actuated computer input device of claim 7, further comprising a signal receiver connected to said computer terminal; and wherein said input device circuit member further comprises a signal transmitter connected to said at least one switch member that is adapted to wirelessly connect with said signal receiver on said computer terminal, to thereby wirelessly send electronic signals to said computer terminal.

* * * * *